US012694481B2

(12) United States Patent
Maul et al.

(10) Patent No.: US 12,694,481 B2
(45) Date of Patent: Jul. 28, 2026

(54) REDUCING ARTIFACTS OCCURRING DUE TO VESSEL OVERLAPS IN A FOUR-DIMENSIONAL ANGIOGRAPHY DATASET

(71) Applicant: Siemens Healthcare GmbH, Erlangen (DE)

(72) Inventors: Noah Maul, Erlangen (DE); Annette Birkhold, Stuttgart (DE)

(73) Assignee: Siemens Healthineers AG, Forchheim (DE)

( * ) Notice: Subject to any disclaimer, the term of this patent is extended or adjusted under 35 U.S.C. 154(b) by 354 days.

(21) Appl. No.: 18/513,914

(22) Filed: Nov. 20, 2023

(65) Prior Publication Data
US 2024/0193737 A1 Jun. 13, 2024

(30) Foreign Application Priority Data
Dec. 13, 2022 (DE) ...................... 10 2022 213 495.8

(51) Int. Cl.
*G06T 5/50* (2006.01)
*A61B 6/00* (2006.01)
(Continued)

(52) U.S. Cl.
CPC ................ *G06T 5/50* (2013.01); *A61B 6/481* (2013.01); *A61B 6/504* (2013.01); *A61B 6/5258* (2013.01);
(Continued)

(58) Field of Classification Search
CPC ...................... G06T 5/50; G06T 7/0016; G06T 2207/10116; G06T 2207/20081;
(Continued)

(56) References Cited

U.S. PATENT DOCUMENTS 9,805,465 B2 * 10/2017 Kyriakou ................ G06T 15/08
10,524,755 B2 * 1/2020 Kowarschik ........... G16H 50/30
(Continued)

FOREIGN PATENT DOCUMENTS

DE 102017200489 A1 7/2018
DE 102019200888 A1 7/2020
DE 102021210860 A1 3/2023

OTHER PUBLICATIONS

Davis, B. et al. "4D Digital Subtraction Angiography: Implementation and Demonstration of Feasibility" American Society of Neuroradiology, vol. 34, No. 10, Oct. 2013, pp. 1914-1921.

*Primary Examiner* — Atiba O Fitzpatrick
(74) *Attorney, Agent, or Firm* — Lempia Summerfield Katz LLC

(57) ABSTRACT

A method is provided for reducing artifacts occurring due to vessel overlaps in a four-dimensional angiography dataset acquired with administration of a contrast agent, wherein distribution data relating to a concentration of the contrast agent in the blood circulatory system is generated at the respective time points for a three-dimensional vessel dataset of a blood circulatory system or for a reduced dataset derived therefrom, e.g., by a trained function. A color intensity of a pixel showing a contrast agent filling state contained in a respective projection image of the blood circulatory system is distributed according to the distribution data at the respective time point of the acquired projection image across voxels of the vessel dataset that lie along a ray associated with the pixel in the backprojection.

14 Claims, 7 Drawing Sheets

(51) Int. Cl.
    *A61B 6/50*          (2024.01)
    *G06T 7/00*          (2017.01)

(52) U.S. Cl.
    CPC .. *G06T 7/0016* (2013.01); *G06T 2207/10116*
    (2013.01); *G06T 2207/20081* (2013.01); *G06T*
    *2207/20224* (2013.01); *G06T 2207/30101*
    (2013.01); *G06T 2207/30172* (2013.01)

(58) Field of Classification Search
    CPC . G06T 2207/20224; G06T 2207/30101; G06T
    2207/30172; G06T 11/008; G06T
    2207/20084; A61B 6/481; A61B 6/504;
    A61B 6/5258; G06N 3/0464; G06N
    3/047; G06N 3/048; G06N 3/084
    See application file for complete search history.

(56)           References Cited

U.S. PATENT DOCUMENTS

| | | | |
|---|---|---|---|
| 2008/0020362 A1* | 1/2008 | Cotin | G09B 23/285 |
| | | | 434/267 |
| 2013/0237815 A1* | 9/2013 | Klingenbeck | A61B 6/4014 |
| | | | 600/431 |
| 2014/0313196 A1* | 10/2014 | Mistretta | G06T 11/008 |
| | | | 345/424 |
| 2014/0376791 A1* | 12/2014 | Heigl | G06T 11/008 |
| | | | 382/128 |
| 2016/0135775 A1* | 5/2016 | Mistretta | G06T 7/0012 |
| | | | 600/419 |
| 2017/0249758 A1* | 8/2017 | Mistretta | A61B 6/504 |
| 2017/0256077 A1* | 9/2017 | Schafer | G06T 11/008 |
| 2018/0071452 A1* | 3/2018 | Sharma | A61M 5/007 |
| 2018/0199905 A1* | 7/2018 | Kowarschik | A61B 6/4441 |
| 2018/0211422 A1* | 7/2018 | Qiu | G06T 5/50 |
| 2020/0013153 A1* | 1/2020 | Kaethner | G06N 3/04 |
| 2020/0237330 A1* | 7/2020 | Birkhold | A61B 6/481 |
| 2020/0281543 A1* | 9/2020 | Sahbaee Bagherzadeh | A61B 6/032 |
| 2020/0375563 A1* | 12/2020 | Regensburger | G06T 7/33 |
| 2021/0015438 A1* | 1/2021 | Sahbaee Bagherzadeh | G06V 10/82 |
| 2021/0219850 A1* | 7/2021 | Birkhold | A61B 5/02014 |
| 2023/0123449 A1* | 4/2023 | Birkhold | G16H 50/50 |
| | | | 606/130 |
| 2024/0428477 A1* | 12/2024 | Salehi | A61B 6/5235 |
| 2025/0061620 A1* | 2/2025 | Salehi | G06T 11/006 |

\* cited by examiner

FIG 1

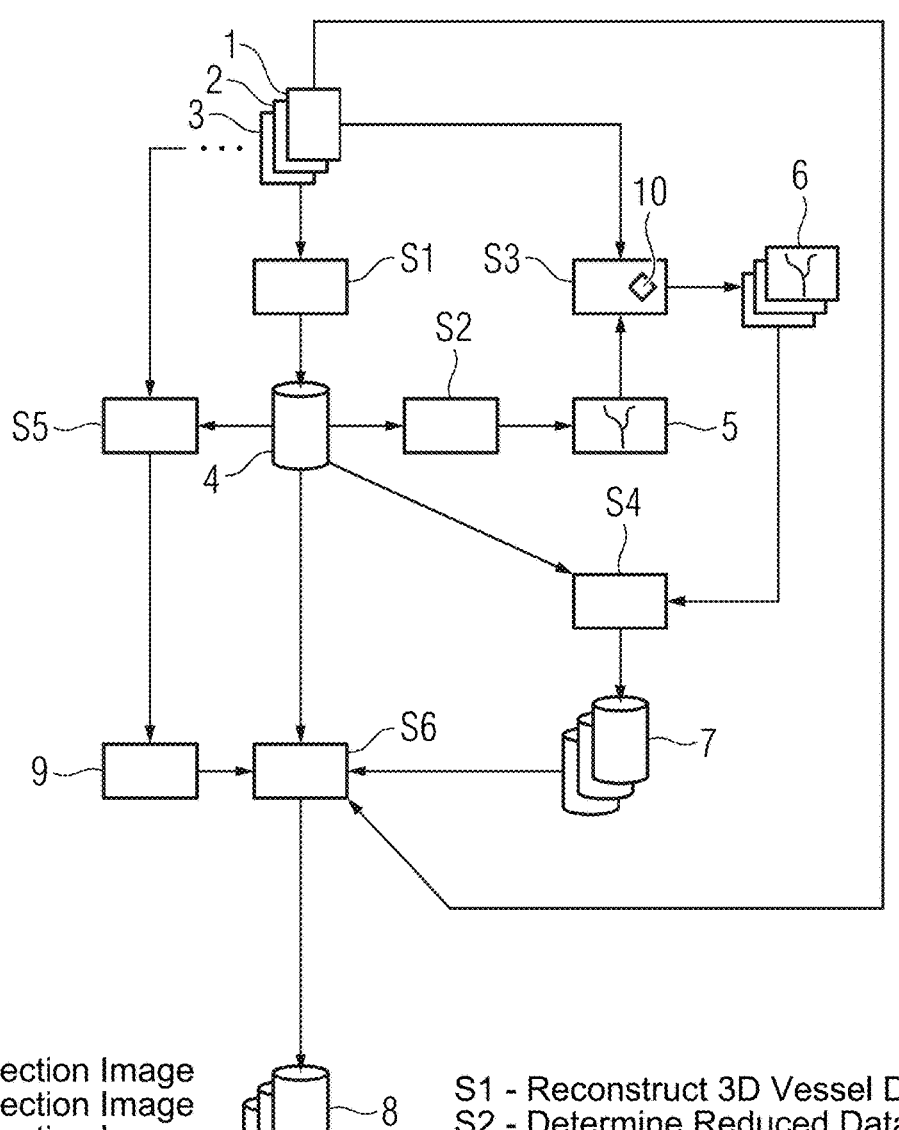

1 - Projection Image
2 - Projection Image
3 - Projection Image
4 - 3D Vessel Dataset
5 - Reduced Dataset
6 - Distribution Data
7 - 3D Distribution Data
8 - 4D Angiography Dataset
9 - Measure of Voxels
10 - Trained Function S1 - Reconstruct 3D Vessel Dataset
S2 - Determine Reduced Dataset
S3 - Generate Distribution Dataset
S4 - Generate 3D Distribution Dataset
S5 - Determine Number of Voxels
S6 - Determine 4D Angiography Dataset 10 - Trained Function
27 - Real Projection Images
28 - Simulated Projection Images
29 - 3D Vessel Dataset
30 - Reduced Dataset
38 - Distribution Data S7 - Reconstruct 3D Vessel Dataset
S8 - Determine Reduced Dataset
S9 - Generate 3D Vessel Dataset
S10 - Training Function

REDUCING ARTIFACTS OCCURRING DUE TO VESSEL OVERLAPS IN A FOUR-DIMENSIONAL ANGIOGRAPHY DATASET

The present patent document claims the benefit of German Patent Application No. 10 2022 213 495.8, filed Dec. 13, 2022, which is hereby incorporated by reference in its entirety.

TECHNICAL FIELD

The disclosure relates to a method for reducing artifacts occurring due to vessel overlaps in a four-dimensional angiography dataset of an acquisition region of interest. The disclosure further relates to a computer-implemented method for providing a trained function, to an image processing device, to a computer program, to an electronically readable data medium, and to a training system.

BACKGROUND

Overlapping vessels are a known problem in digital subtraction angiography (DSA). A major step in the direction of reliable and readily interpretable images was the development of four-dimensional digital subtraction angiography. This modality entails using an X-ray device, (e.g., an X-ray device having a C-arm), to acquire, in the course of one or more rotations, two-dimensional projection images of the acquisition region of interest of the blood circulatory system of the patient taken at different projection angles at respective time points in a specific time interval, while the contrast agent flows through the blood circulatory system in the acquisition region. Digital subtraction angiography projection images are obtained by subtracting a mask image acquired without contrast agent, while a subtraction may also be carried out for respective reconstructed three-dimensional image datasets. While it was known in the early days of digital subtraction angiography how to generate multiple three-dimensional image datasets succeeding one another in time by using digital subtraction angiography projection images acquired in a specific time interval in order to reconstruct therefrom a three-dimensional partial image dataset, there existed in the meantime more novel approaches capable of delivering better image quality as well as a better temporal resolution.

One of these approaches has been described in an article by B. Davis et al. titled "4D Digital Subtraction Angiography: Implementation and Demonstration of Feasibility," DOI: 10.3174/ajnr.A3529. There, it is proposed initially using an in particular large proportion of the digital subtraction angiography projection images showing at least largely filled vessels to reconstruct a non-time-resolved three-dimensional vessel dataset showing the entire blood circulatory system in the acquisition region, which 3D dataset forms the basis for a continuous updating of the voxel values by multiplicative embedding of the time information of the, in particular normalized, digital subtraction angiography projection images, with the result that a series of time-resolved 3D images, i.e., the four-dimensional angiography dataset, or at least a partial image dataset is produced. In other words, the vessel dataset is ultimately used to constrain the reconstruction of the angiography dataset which integrates the temporal information from the digital subtraction angiography projection images. A multiplicative backprojection is therefore performed. This may be understood in the sense that vessels lying on the ray of a pixel of a projection image and showing a contrast agent filling state by virtue of its color intensity (voxels marked as vessels) are highlighted as filled with contrast agent at the time point of the acquisition of the projection image.

However, this use of image acquisitions in a single plane and of multiplicative backprojection in the four-dimensional image reconstruction may lead to problems whenever a vessel overlap is present along the rays of the current projection image. More precisely, the multiplicative backprojection of a two-dimensional projection image into a static three-dimensional constraining image, i.e., the vessel dataset, leads (without additional regularization) to a non-plausible highlighting of vessels because the color intensity of at least one pixel of the two-dimensional projection image cannot be unequivocally assigned to one of the overlapping vessel voxels that is to be highlighted. This therefore means that an algorithm of this type may generate artifacts due to vessel overlap by erroneously highlighting certain voxels of vessel segments. For the user, for example a physician attempting a diagnosis, this means that the image quality and the clinical significance of this four-dimensional imaging suffer on that account.

In order to reduce the number of overlap artifacts, it has already been proposed in the case of multiplicative backprojection for determining the three-dimensional partial image datasets that are assigned to different time points to determine at the same time a likewise four-dimensional confidence map as a confidence dataset that describes the vessel overlap along relevant rays used. In this process, a pronounced vessel overlap may be assigned the confidence value 0 and a nonexistent vessel overlap may be assigned the confidence value 1. Confidence values of the confidence dataset may be determined by "counting" the vessels, in particular by integration along the ray and comparison with at least one threshold value. On the basis of the four-dimensional confidence dataset describing the vessel overlap, it is possible to interpolate unreliable intensity values of the provisional four-dimensional angiography dataset between sufficiently reliable neighboring values in time and consequently replace the less reliable values, for example, values falling below a threshold value for the confidence value.

It has been found, however, that there is still potential for improvement with regard to this approach with the elimination of the image quality problem due to vessel overlap artifacts. In particular, it is currently not possible to distribute the color intensity of the pixel across the voxels in such a way that the latter may be highlighted with a corresponding concentration of the contrast agent.

DE 10 2017 200 489 A1 describes a method in which, in a plausibility checking step, vessel segments represented as filled with contrast agent in partial image datasets of the angiography dataset assigned to all individual, different time points in the covered time period are checked against a plausibility check criterion checking for the presence of a contrast-agent-filled connection to an admissible source point, wherein a corrected partial image dataset is determined containing only the vessel segments that satisfy the plausibility check criterion.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object underlying the disclosure is to provide an improved and faster reducing vessel overlap artifacts occurring due to overlapping of vessels. Irrespective of the grammatical gender of a particular term, individuals having male, female, or other gender identity are also included.

In order to achieve this object, it is provided in a method of the type cited in the introduction in particular that for the three-dimensional vessel dataset or for a reduced dataset derived therefrom, data relating to a distribution of a concentration of the contrast agent in the blood circulatory system is generated at the respective time points in the time interval. Further, it is provided that a color intensity of a pixel showing a contrast agent filling state in a respective projection image of the projection images is distributed according to the distribution data at the respective time point of the acquired projection image across voxels of the vessel dataset which lie along a ray associated with the pixel in the backprojection.

The four-dimensional angiography dataset covers a particular time period of the characteristic curve of the contrast agent concentration in the acquisition region by a time series of three-dimensional partial image datasets. This means that each picture element of the four-dimensional angiography dataset corresponds not only to a volume element of a vessel, in particular a voxel, but each of the picture elements contains a contrast agent concentration characteristic curve over the time period. In particular, there may be produced from the four-dimensional angiography dataset partial image datasets describing contrast agent concentration states corresponding to different time points within the time period, in particular one 3D image in each case at the time points. A time point in this context is to be understood as a subsection of the time period. In particular, depending on the temporal resolution of the four-dimensional angiography dataset, a time point may cover a certain time interval which may correspond, for example, to the smallest resolvable unit of time or to a multiple thereof.

The three-dimensional vessel dataset may be reconstructed from the projection images. In particular, for reasons of simplification or for improved visualization, a base dataset, which may henceforth contain only image values above a specific threshold value, may be derived from the vessel dataset. The base dataset may also be understood by the vessel dataset, or the acts described herein may also be applied for the base dataset instead of the vessel dataset.

The three-dimensional vessel dataset may digitally image the acquired three-dimensional blood circulatory system so that the blood circulatory system may be displayed by the vessel dataset on a corresponding display device and/or be used for fluid dynamic calculations. In particular, the vessel dataset may image blood vessel walls of the blood circulatory system, within which vessel walls a blood flow is made possible. In other words, the possible blood flow, in particular a blood flow mixed with contrast agent, may be limited to a volume within the blood vessel walls. Based on this restriction and, if applicable, further boundary conditions, a computing unit may generate data relating to the distribution of the concentration of the contrast agent at the respective time points such that the distribution becomes forecastable, in particular predictable. In order to generate the data, boundary conditions, (e.g., in the form of a source of the contrast agent, an amount of the contrast agent, a heart rate, a blood flow rate, an injection rate, or the like), may be defined.

In a possible embodiment variant, the distribution of the concentration of the contrast agent may therefore be generated virtually regardless of information in the projection images concerning the concentration of the contrast agent, but solely based on the blood circulatory system imaged by the vessel dataset.

Instead of being generated for the three-dimensional vessel dataset, the distribution data may also be generated for the reduced dataset of the blood circulatory system imaged by the reduced dataset, which in particular visualizes the blood circulatory system in simplified form in order to reduce a required computing power and computing time of the computing unit.

The distribution data may be generated as a three-dimensional concentration image dataset. In particular, the distribution data may be available in each case at a time point among the respective time points. The data may be generated or predicted as a four-dimensional concentration image dataset that images the variation with respect to time of the contrast agent concentration in the blood flow within the blood circulatory system.

The generated distribution data may only contain a prediction of the distribution that is meaningful in terms of fluid dynamics, but which cannot yet image the actual distribution of the contrast agent concentration in the actually acquired blood circulatory system in the time interval. Rather, the generated distribution data may be drawn upon for at least one further method act.

In particular, it is not provided that the distribution data provides absolute values for the concentration of the contrast agent in a respective voxel of the blood circulatory system imaged by the vessel dataset, but rather provides relative values of the concentration levels of the individual voxels with respect to one another. In other words, the distribution may be understood as a distribution key by which a sum of concentrations, acquired for example based on the color intensity of a pixel of a projection image, may be distributed across the voxels.

In an act of the method, the color intensity of a pixel showing a contrast agent filling state of a respective projection image of the projection images of the acquired projection image is distributed across voxels of the vessel dataset which lie along a ray associated with the pixel in the backprojection. In particular, the color intensity of each or at least of a plurality of pixels of the respective projection image showing contrast agent filling is distributed. In particular, this happens for each projection image or at least for a plurality of the acquired digital subtraction angiography projection images.

In particular, the color intensity may also be understood as color depth or color strength or as a measure, in particular expressed as a percentage, for the intensity of a color perception. For example, a pixel representing the color white may have a color intensity of 0%, a respective gray tone a color intensity of 1% to 99%, and the color black a color intensity of 100%. In particular, the color intensity may correspond to a brightness value of a grayscale image. As a result of the assignment of the color intensity to a voxel lying on the ray, it is possible to infer in particular the concentration of the contrast agent in the voxel. The color intensity may be proportional to the concentration of the contrast agent in the voxel. If only one voxel is located on the ray, the color intensity may be unequivocally assigned to that voxel.

When there are multiple voxels on the associated ray of the pixel, the color intensity may be proportional to a sum total of the concentrations of the contrast agent in the respective voxel. In a backprojection of the intensity onto the voxels, it has previously been possible to conclude that the color intensity may not be distributed as unequivocally assignable across the voxels because the sum may be yielded from a plurality of combinations of summands. For example, it may transpire in this case that a voxel has been assigned a color intensity, and consequently a concentration, even though in reality the voxel contains no contrast agent, with the result that artifacts occur in the angiography dataset due to the vessel overlap. It may likewise become apparent, for example, that the color intensity has been allocated across a plurality of voxels in an incorrect ratio. For example, it may have happened that in the case of a color intensity of the pixel of 70%, 35% has been assigned to each of two associated voxels even though, for a real representation, it would have been necessary to assign 20% to a first voxel, for example, and 50% to a second voxel, with the result that incorrect concentrations of the contrast agent were represented in the voxels.

The color intensity is assigned to the voxels in accordance with the generated, in particular predicted, distribution data at the respective time point of the acquired projection image. Accordingly, the color intensity may advantageously be distributed across the voxels in an improved manner and the concentration of the contrast agent may be inferred on the basis of the percentage of the color intensity of the voxels. Thus, artifacts in the angiography dataset due to vessel overlap are considerably reduced. In particular, the color intensity may be distributed across the voxels unequivocally, reliably, and reproducibly in accordance with the distribution key. Advantageously, the color intensity may be distributed across the voxels as appropriate with a high probability. Furthermore, a resource- and time-consuming postprocessing due to implausible concentrations of the angiography dataset may be dispensed with. The acquisition of the angiography dataset may be completed faster as a result.

The method may be executable as a computer-implemented or at least partially computer-implemented process, in particular by an image processing device.

By a computing unit may be understood in particular a data processing device which contains a processing circuit. The computing unit may therefore process in particular data for performing computational operations. If necessary, these may also include operations for performing indexed accesses to a data structure, (e.g., a lookup table (LUT)).

The computing unit may contain one or more computers, one or more microcontrollers, and/or one or more integrated circuits, (e.g., one or more application-specific integrated circuits (ASICs)), one or more field-programmable gate arrays (FPGAs), and/or one or more single-chip systems (SoCs: system on a chip). The computing unit may also contain one or more processors, e.g., one or more microprocessors, one or more central processing units (CPUs), one or more graphics processing units (GPUs) and/or one or more signal processors, in particular one or more digital signal processors (DSPs). The computing unit may also include a physical or virtual cluster of computers or other of the cited units.

In different exemplary embodiments, the computing unit contains one or more hardware and/or software interfaces and/or one or more memory units.

An embodiment variant of the method provides that a number of voxels lying on the ray is determined from the vessel dataset, e.g., for all pixels or at least for a plurality of the pixels. This information may be determined as an output variable by a processing unit from the three-dimensional vessel dataset as an output variable.

The voxels or the voxel may be assigned a measure for the determined number, (e.g., a confidence value), a count being taken of how many vessels lie along a ray considered in the multiplicative backprojection in order to assign a lower confidence value in the case of a larger assumed number of vessels.

It may be provided that the color intensity of the pixel is distributed according to the distribution data only if the measure falls below a predefined value or lies within a predefined value range.

For example, the predefined value may be 0.9. For example, the measure may have a value of 1 if it is determined that precisely one voxel lies on the ray. In this example, the color intensity may be assigned directly to the one voxel without the distribution data. The method may be simplified and speeded up as a result.

In a further example, the measure may have a value of 0.5 if it is determined or assumed with at least a certain probability that a plurality of voxels lie on the ray. In this case, it may be provided that the color intensity of the pixel is distributed according to the distribution data.

An embodiment variant of the method provides that vessel centerlines, (e.g., central lines), of the blood circulatory system are determined from the three-dimensional vessel dataset or from the base dataset as a reduced dataset, e.g., as data relating to the vessel centerlines. The vessel centerlines may be understood as those lines that connect respective center points of cross-sectional areas of the blood vessel segments of the blood circulatory system to one another. The vessel centerlines may be formed in particular one-dimensionally in a three-dimensional space. Accordingly, the vessel centerlines may image the blood circulatory system in a simplified manner. For further simplification, only a specific set of center points may be connected to one another relative to the vessel centerline, for example, by straight-lined connection of center points spaced apart at a specific distance. The data relating to the vessel centerlines may be determined in an integration act, (e.g., extracted by integration), by a computing unit from the vessel dataset or from the base dataset. The distribution may therefore be effectively estimated or predicted.

The distribution data relating to the concentration of the contrast agent in the blood circulatory system at the respective time points may be generated for the vessel centerlines. This data includes a time-resolved distribution of the concentration or a time-dependent characteristic curve of the distribution.

Generating the distribution across the one-dimensional vessel centerlines of the reduced dataset instead of across the three-dimensional blood circulatory system of the vessel dataset may considerably speed up the method act and significantly reduce a computing time. The method is thus rendered much more efficiently without relevant information being lost in the process. In particular, the distribution data relating to the contrast agent concentration of the extracted vessel centerlines may be sufficient for the method in order to enable the color intensity to be distributed across the voxels in an improved and simplified manner without the appearance of artifacts.

An embodiment variant of the method provides that the distribution data relating to the concentration of the contrast agent for the vessel centerlines is extrapolated onto the three-dimensional vessel dataset, e.g., onto the blood circulatory system imaged by the vessel dataset. In particular, the respective time-resolved concentrations of the respective points of the vessel centerlines may be extrapolated in a suitable manner onto the cross-sectional areas of the blood vessel segments of the blood circulatory systems such that a three-dimensional time-resolved distribution is generated from the one-dimensional time-resolved distribution. This may be performed in an extrapolation act by a computing unit. By this act, reliable data for the three-dimensional time-resolved distribution of the contrast agent concentration may be generated in a simplified manner. Based on the extrapolated distribution data, the color intensity of the pixel may therefore be distributed in an improved manner across the voxels according to the extrapolated distribution data, in particular at a higher resolution across the vessel cross-section.

An embodiment variant of the method provides that the distribution data relating to the concentration of the contrast agent is generated as output data of a trained function. The trained function may be based on an artificial neural network (ANN), e.g., having at least one convolutional layer. In particular, the trained function may be based on a generic inverse algorithm. In particular, a computing unit may be embodied to apply the trained function in the generation act.

The trained function may be trained in such a way that it is suitable for generating, providing, or predicting realistic and meaningful distribution data relating to the concentration of the contrast agent as output data. The trained function may be trained, in particular provided, by a training system by the computer-implemented method for training the trained function.

The trained function may be applied to the projection images and the three-dimensional vessel dataset or the reduced dataset as input data. In other words, the projection images are first input data of the trained function, just as the vessel dataset or the base dataset or the reduced dataset, (e.g., the vessel centerlines), is the second input data of the trained function. The projection images may therefore be taken into account as well in the generation of the distribution data. The distribution may be predicted extremely precisely and individually as a result. Furthermore, by using the trained function the computing unit is able to generate the distribution data extremely quickly, robustly, and with less computing power.

An alternative embodiment variant of the method to the trained function provides that the distribution data relating to the concentration of the contrast agent is generated as output data of a hemodynamic simulation of a virtual blood flow virtually mixed with a contrast agent in the blood circulatory system reconstructed by the computing unit by the vessel dataset, for example, by a CFD solver. A CFD solver may refer to a computer program configured to solve a fluid mechanics problem with numeric methods of computational fluid dynamics (CFD).

In particular, multiple boundary conditions, (e.g., a heart rate, blood flow rate, injection rate, and further biometric data), may be modeled for the simulation. Alternatively, or additionally, clinically measured hemodynamic parameters that correspond to the image datasets or may be determined therefrom may also be used.

In certain embodiments, the trained function is provided by a computer-implemented method that is described hereinbelow.

For application cases or application situations that may arise with the method, and which are not explicitly described here, an error message and/or a request to input a user feedback response may be output and/or a default setting and/or a predetermined initial state may be set.

A computer-implemented method for providing a trained function is also disclosed herein. The computer-implemented method includes receiving input training data including: (a) two-dimensional digital subtraction angiography projection images showing a blood circulatory system and having been acquired at respective time points in a specific time interval, and (b) a three-dimensional vessel dataset of the blood circulatory system, or a reduced dataset derived from the vessel dataset. The method further includes receiving output training data including distribution data relating to a concentration of the contrast agent in the blood circulatory system imaged by the vessel dataset or reduced dataset at the respective time points for the three-dimensional vessel dataset or for the reduced dataset, wherein the output training data is related to the input training data. The method further includes training a function based on the input training data and the output training data, wherein output data is generated by applying the function to the input training data and parameters of the function are adjusted based on a comparison of the output data with the output training data. The method further includes providing the trained function.

The input training data may be received by a first training interface of a training system, and the output training data may be received by a second training interface.

The acquired projection images may correspond to projection images acquired in real-world practice. Alternatively, the acquired projection images may be simulated, e.g., in such a way that the projection images exhibit the properties of real projection images of a real subtraction angiography procedure, e.g., have different time points at different acquisition angles of an image acquisition.

The three-dimensional vessel dataset may be reconstructed, for example, from acquired digital subtraction angiography projection images of the real blood circulatory system. Alternatively, the three-dimensional vessel dataset may be modeled such that a virtual, yet realistic blood circulatory system may be imaged. In particular, a plurality of vessel datasets may be generated as input training data in this way.

Alternatively to the vessel dataset, the reduced dataset of the blood circulatory systems derived therefrom may be received as an input training dataset.

The function may be based on an artificial neural network (ANN), e.g., having at least one convolutional layer. In particular, the function may be based on a generic inverse algorithm. In particular, the training system may be configured to train the function. The function may be trained in such a way that it is suitable as a trained function for generating or predicting realistic and meaningful distribution data relating to the concentration of the contrast agent as output data.

An error of the function may be determined by comparison of the output data with the output training data. For example, a metric known as a cost function may be calculated in order to quantify the error. For example, the parameters of the function may be adjusted by a known algorithm in such a way that the cost function is minimized, in particular iteratively.

An embodiment variant of the computer-implemented method provides that the distribution of the concentration of the contrast agent in the blood circulatory system, (e.g., the output training data), is generated as output data of a hemodynamic simulation of a virtual blood flow mixed with a contrast agent in the blood circulatory system imaged by the vessel dataset. This advantageously enables extremely precise and robust output training data to be generated, which may realistically simulate the actual distribution of the concentration. Reliable output training data may advantageously be generated as a result.

In particular, the vessel dataset may be reconstructed or modeled from real projection images.

For the purposes of the simulation, multiple boundary conditions, (e.g., a heart rate, blood flow rate, injection rate, and further biometric data), may be modeled. Alternatively, or additionally, clinically measured hemodynamic parameters that correspond to the image datasets or may be determined therefrom may also be used.

An embodiment variant of the computer-implemented method provides that the projection images are generated as further output data of the hemodynamic simulation. The generated projection images may simulate real projection images acquired in a real digital subtraction angiography procedure, in particular in such a way that these exhibit the properties of real projection images of a real subtraction angiography procedure, e.g., have different time points at different acquisition angles of an image acquisition.

Both the projection images and the distribution data relating to the concentration of the contrast agent may be generated as output data from the same hemodynamic simulation and used as training data for training the function. By this, it may advantageously be provided firstly that the training data is consistent in itself and that the function may be trained effectively and in a targeted manner. Secondly, only a single hemodynamic simulation is necessary in order to provide both the distribution data and the projection images. Valuable resources, (e.g., time and computational overhead), may be saved as a result.

An embodiment variant of the computer-implemented method provides that vessel centerlines of the blood circulatory system are determined as a reduced dataset from the three-dimensional vessel dataset, the distribution data relating to the concentration of the contrast agent in the blood circulatory system being provided for the vessel centerlines.

Generating the distribution across the one-dimensional vessel centerlines of the reduced dataset instead of across the three-dimensional blood circulatory system of the vessel dataset may considerably speed up the training of the function and significantly reduce a computing time. The training is consequently rendered much more efficient. In particular, the distribution data relating to the contrast agent concentration of the extracted vessel centerlines may be sufficient for the method in which the trained function is applied.

Unless indicated otherwise, all the acts of the computer-implemented method may be carried out by the training system, which includes at least one (training) computing unit. In particular, the at least one computing unit is configured or adapted for performing the acts of the computer-implemented method. For this purpose, the at least one computing unit may store a computer program containing commands which, when executed by the at least one computing unit, cause the at least one computing unit to perform the computer-implemented method.

Further embodiment variants of the computer-implemented method for training the function follow directly from the various embodiments of the method that applies the trained function, and vice versa. In particular, individual features and corresponding explanations as well as advantages in respect of the various embodiment variants in relation to the method which applies the trained function may be applied analogously to corresponding embodiment variants of the computer-implemented method for training the function.

For application cases or application situations that may arise with the computer-implemented method and that are not explicitly described here, an error message and/or a request to input a user feedback response may be output and/or a default setting and/or a predetermined initial state may be set.

In another aspect of the disclosure, an image processing device is provided. The image processing device includes a determination unit configured to determine a four-dimensional angiography dataset of an acquisition region of interest of a blood circulatory system of a patient. The determination unit includes a reconstruction subunit for reconstructing a three-dimensional vessel dataset of the blood circulatory systems from two-dimensional digital subtraction angiography projection images showing the blood circulatory system and having been acquired at respective time points in a specific time interval, as well as a backprojection subunit configured to determine the angiography dataset by backprojection of the projection images into the vessel dataset. In addition, the image processing device includes a computing unit configured to generate distribution data relating to a concentration of the contrast agent in the blood circulatory system at the respective time points in the time interval for the three-dimensional vessel dataset or for a reduced dataset derived therefrom, as well as a distribution unit configured to distribute a color intensity of a pixel showing a contrast agent filling state contained in a respective projection image of the projection images according to the distribution data at the respective time point of the acquired projection image across voxels of the vessel dataset that lie along a ray associated with the pixel in the backprojection.

Further embodiment variants of the image processing device follow directly from the various embodiments of the method for reducing artifacts, and vice versa. In particular, individual features and corresponding explanations as well as advantages in respect of the various embodiment variants in relation to the method for reducing artifacts may be applied analogously to corresponding embodiment variants of the image processing device. In particular, the image processing device is embodied or programmed to perform a method for reducing the artifacts. In particular, the image processing device performs the method for reducing artifacts.

By a further aspect, a computer program is provided that performs the acts of the method for reducing artifacts when the computer program is executed on an image processing device.

The computer program may be loaded directly into a memory of an image processing device and has program means for performing the acts of a herein-described method for reducing artifacts when the computer program is executed in the image processing device.

By a further aspect, an electronically readable data medium is provided on which a computer program is stored.

The computer program may be stored on the electronically readable data medium, which therefore includes electronically readable control information stored thereon that includes at least one computer program and is embodied in such a way that when the data medium is used in an image processing device, the control information performs a herein-described method for reducing artifacts. The electronically readable data medium may be a non-transitory data medium, for example, a CD-ROM.

A training system is provided by a further aspect. The training system includes a first training interface configured to receive input training data including two-dimensional digital subtraction angiography projection images showing a blood circulatory system and having been acquired at respective time points in a specific time interval, and a three-dimensional vessel dataset of the blood circulatory system, or a reduced dataset derived therefrom.

The training system further includes a second training interface configured to receive output training data including data distribution relating to a concentration of a contrast agent in the blood circulatory system at the respective time points in the time interval for the three-dimensional vessel dataset or for the reduced dataset, the output training data being related to the input training data.

The training system further includes a training computing unit configured to train a function based on the input training data and the output training data, wherein output data is generated by applying the function to the input training data and parameters of the function are adjusted based on a comparison of the output data with the output training data.

The training system further includes a third training interface configured to provide the trained function.

Further embodiment variants of the training system follow directly from the various embodiments of the method for providing the trained function, and vice versa. In particular, individual features and corresponding explanations as well as advantages in respect of the various embodiment variants in relation to the method for providing the trained function may be applied analogously to corresponding embodiment variants of the training system. In particular, the training system is embodied or programmed to perform a method for providing the trained function. In particular, the training system performs the method for providing the trained function.

By a further aspect, a second computer program is provided that is configured to perform the acts of the method for providing the trained function when the computer program is executed on a training system.

The second computer program may be loaded directly into a memory of a training system and has program code for performing the acts of a herein-described method for providing the trained function when the second computer program is executed in the training system.

By a further aspect, a second electronically readable data medium is provided on which a second computer program is stored.

The second computer program may be stored on the second electronically readable data medium, which therefore includes electronically readable control information stored thereon which includes at least one second computer program and is embodied in such a way that when the data medium is used in a training system, the control information performs a herein-described method for providing the trained function. The electronically readable data medium may be a non-transitory data medium, for example, a CD-ROM.

Further features of the disclosure are apparent from the claims, the figures, and the description of the figures. The features and feature combinations cited above in the description, as well as the features and feature combinations cited below in the description of the figures and/or shown in the figures, may be encompassed by the disclosure not only in the combination disclosed in a given case but also in other combinations. In particular, embodiments and feature combinations that do not possess all the features of an originally formulated claim may also be included in the disclosure. Furthermore, embodiments and feature combinations that go beyond the feature combinations set forth in the back-references of the claims or diverge therefrom may be encompassed by the disclosure.

BRIEF DESCRIPTION OF THE DRAWINGS

FIG. 1 depicts a flowchart of an embodiment of a method for reducing artifacts.

DETAILED DESCRIPTION

Figure 2:
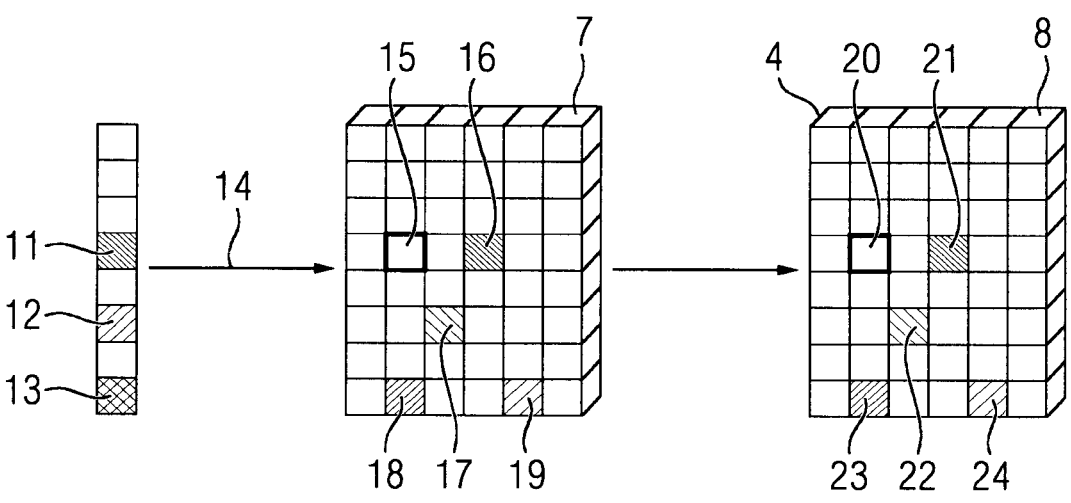
FIG. 2 depicts an example of a diagram intended to explain the distribution of the color intensity of a pixel across voxels.

FIG. 1 shows a flowchart of an exemplary embodiment of the method for reducing artifacts. Taken as the starting point in this case are two-dimensional digital subtraction angiography projection images 1, 2, 3, e.g., acquired from different projection directions by an angiography device 40 having a C-arm 41 during one revolution or multiple revolutions, wherein a mask image acquired without contrast agent from the respective direction may be subtracted in order to obtain the digital subtraction angiography projection images 1, 2, 3. For example, around 90 projection images 1, 2, 3 are acquired during one revolution. In other exemplary embodiments, a subtraction of a three-dimensional reconstructed mask image dataset may also be performed following a reconstruction.

The projection images 1, 2, 3 show an acquisition region of interest of a blood circulatory system 25, (e.g., a blood vessel tree of a patient), and, in their temporal sequence, the propagation of a contrast agent which has been administered accordingly in the acquisition region of interest. It is known in this case to employ a relatively long administration of contrast agent, (e.g., of 7 seconds), in order to obtain a greater number of two-dimensional projection images 1, 2, 3 when the blood circulatory system of the patient is almost completely filled in the acquisition region of interest. A corresponding portion of the projection images 1, 2, 3 is used in act S1 in order to reconstruct herefrom in the customary manner a three-dimensional vessel dataset 4 of the highest possible quality that shows the blood circulatory system 25 in its entirety in the acquisition region. The vessel dataset 4 may contain 3D vessel geometries, the vessel walls of which may serve as a constraining geometry for further method acts.

Figure 3:
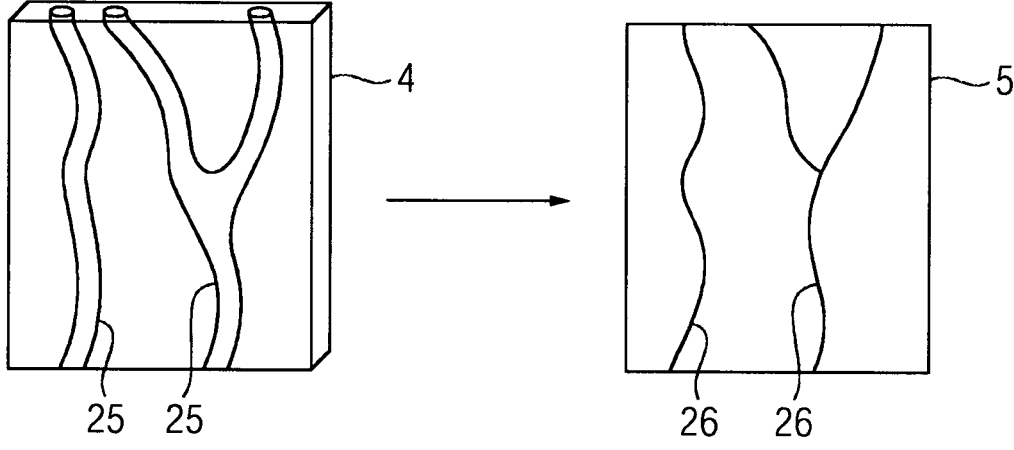
FIG. 3 depicts an example a diagram intended to explain the reduction of the vessel dataset to a reduced dataset.

In an exemplary embodiment, in act S2, a reduced dataset 5 may be determined from the three-dimensional vessel dataset 4. To illustrate this, an exemplary embodiment is shown in FIG. 3 indicating how a reduced dataset 5 may be understood. In this example, the blood circulatory system 25, which is imaged by the vessel dataset 4, is reduced to vessel centerlines 26 that represent the blood circulatory system in simplified form by the reduced dataset 5, (e.g., as a one-dimensional line that connects a specific number of center points of vessel cross-sections of the blood circulatory system 25 to one another).

Based on the reduced dataset 5 and the projection images 1, 2, 3 as input data, the distribution data 6 relating to the concentration of the contrast agent in the blood circulatory system 25 may be generated in act S3 for the vessel centerlines 26, which are in particular time-resolved so that a variation with respect to time of the contrast agent concentration distribution is given. For example, a respective contrast agent concentration is assigned in each case in the distribution data 6 to a point or a section of the vessel centerlines 26 at a respective time point.

In one exemplary embodiment, in act S3, the distribution data 6 relating to the concentration of the contrast agent may be generated as output data 6 of a trained function 10. Exemplary embodiments of the trained function 10 are described by FIG. 6 and FIG. 7, as well as by the explanations thereto. The trained function 10 may be trained by a computer-implemented method, as illustrated and described in FIG. 5 and the explanation thereto.

Alternatively, the data 6, 7 may be generated as output data of a hemodynamic simulation of a virtual blood flow virtually mixed with a contrast agent in the blood circulatory system 25 reconstructed by the vessel dataset 4.

In an exemplary embodiment, in act S4, the distribution data 6 relating to the concentration of the contrast agent for the vessel centerlines 26 may be extrapolated onto the three-dimensional vessel dataset 4, (e.g., by a computing unit), such that the output data of act S4 may be output as three-dimensional distribution data 7 relating to the concentration of the contrast agent.

In an exemplary embodiment, in act S6, the projection images 1, 2, 3 and the three-dimensional distribution data 7 may be used as input data in order to determine the four-dimensional angiography dataset 8. In this process, a color intensity of a pixel 11 of a respective projection image 1 of the projection images 1, 2, 3 showing a contrast agent filling is distributed according to the three-dimensional distribution data 7 at the respective time point of the acquired projection image 1 across voxels 20, 21 of the vessel dataset 4 that lie along a ray 14 associated with the pixel 11 in the backprojection. In particular, this act may be performed for all of the projection images or for at least a plurality of the projection images 1, 2, 3, as well as for all of the pixels or for a plurality of pixels of a respective projection image such that the four-dimensional angiography dataset 8 may be determined in full.

For this purpose, an exemplary embodiment is shown in FIG. 2 illustrating how act S6 may be performed. To simplify the illustration, a one-dimensional pixel strip of an actually two-dimensional projection image is shown which includes three pixels 11, 12, 13, each of which shows a contrast agent filling. The color intensity of the contrast agent filling is intended to be represented here in each case by the different hatching. For example, the first pixel 11 shows a high color intensity, the second pixel 12 a low color intensity, and the third pixel 13 a medium color intensity. All the other pixels of the pixel strip show no color intensity.

For further simplification, the three-dimensional distribution data 7 relating to the contrast agent concentration is shown in the exemplary embodiment as a layer associated with the pixel strip. The data 7 may on the one hand image a voxel 15-19 of the blood circulatory system 25 as a limiting volume. The voxels 15-19 may be associated with the voxels of the vessel dataset 4 or correspond to these. On the other hand, one of the voxels 15-19 in each case may be assigned information about a respective concentration of the contrast agent such that a corresponding distribution of the concentration may be visualized. In this example, as represented by the hatching, the first voxel shows no concentration, the second voxel 16 a high concentration, the third and fourth voxels 17, 18 a medium concentration, and the fifth voxel 19 a low concentration.

The voxels 15-19 of the data 7 or of the vessel dataset 4 may be associated with voxels 20-24 of the angiography dataset 8 or correspond to these. In this example, the voxels 15 and 16 or the voxels 20 and 21 lie on the ray 14, which is associated with the pixel 11. Without the information about the respective concentration in the voxels 15 and 16 from the data 7, the color intensity may not be unequivocally distributed to the voxels 20 and 21, with the result that artifacts would be generated in the angiography dataset 8. Based on the data 7, however, the color intensity of the pixel 11 may be unequivocally distributed across the voxels 20 and 21 according to the distribution of the concentration, with the result that the appearance of artifacts may be prevented or at least substantially reduced. In this example, the color intensity of the pixel 11 is distributed in full to the voxel 21 according to the data 7, whereas no color intensity is apportioned to the voxel 20. Based on the color intensities of the voxels 21-24 of the angiography dataset 8, it is now possible directly to infer the concentration of the contrast agent in the blood circulatory system 25. In particular, the described acts are performed for all or at least a plurality of the projection images 1,2,3 that were acquired at a respective time point such that the angiography dataset 8 may contain time-resolved information about the contrast agent concentration.

Returning to FIG. 1, act S5 may optionally be performed in an exemplary embodiment, which act has recourse to the projection images 1, 2, 3 and the vessel dataset 4 as input data. A number of voxels 20 and 21 lying on the ray 14 may be determined in this case from the vessel dataset 4. The voxels 20 and 21 may thereupon be assigned a measure 9 for the determined number, in particular a confidence value. It may be provided that the color intensity of the pixel 11 is distributed according to the distribution data 7 only if the measure 9 falls below a predefined value. In this example, shown in FIG. 2, the two voxels 20 and 21 lie on the ray 14, so the measure 9 of the voxels 20 and 21 may fall below the predefined value, and the color intensity of the pixel 11 may be assigned accordingly to the voxels 20 and 21 according to the data 7. Alternatively, the color intensity may be assigned directly to the voxel, for example, the color intensity of the pixel 12 to the voxel 22.

Figure 4:
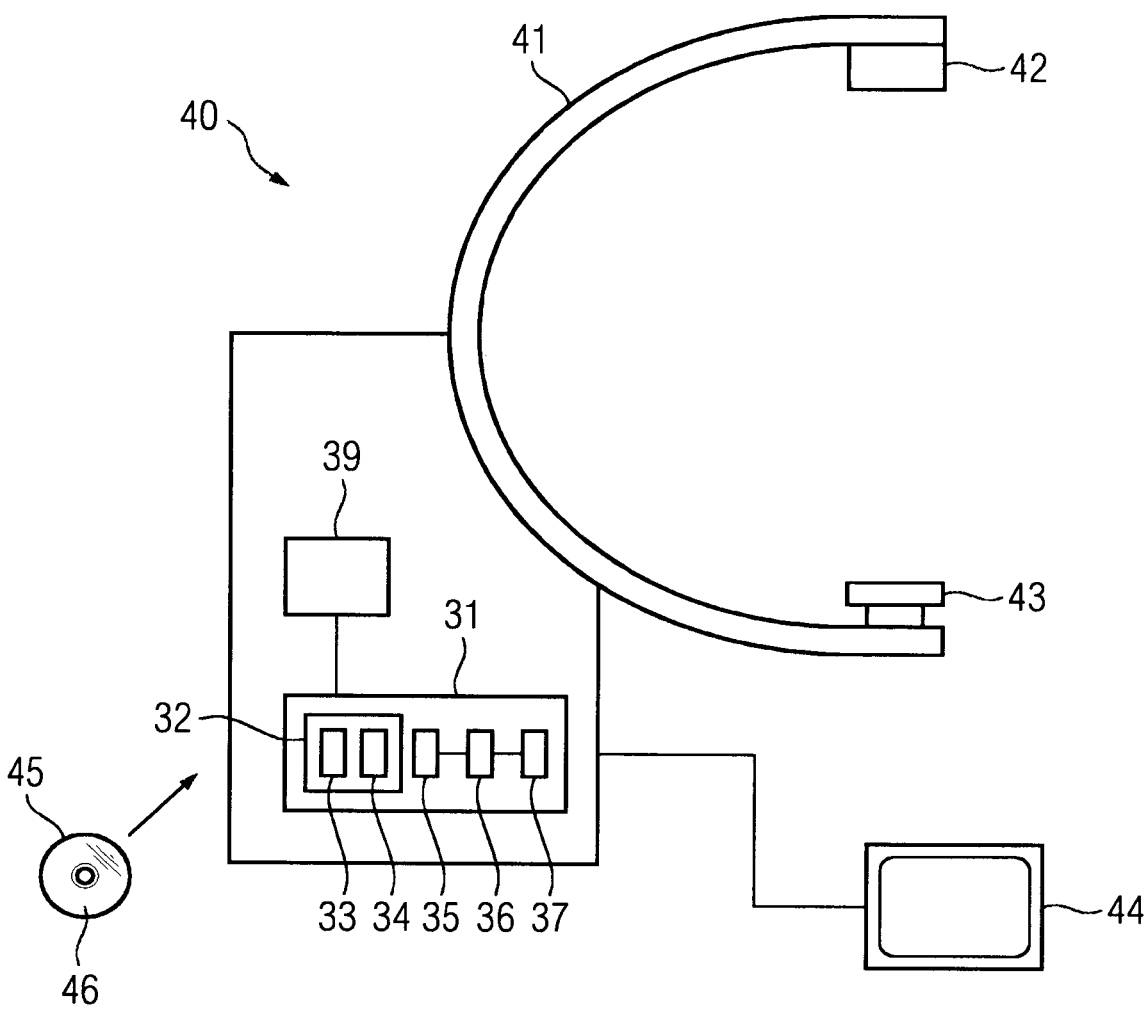
FIG. 4 depicts a schematic representation of an embodiment of an angiography device.

FIG. 4 shows a schematic view of an exemplary embodiment of an angiography device 40 that may be used within the scope of the method for reducing artifacts. In addition to a C-arm 41, on which an X-ray emitter 42 and an X-ray detector 43 are arranged opposite each other and by which the projection images 1, 2, 3 may be acquired, as well as an associated control unit 39 for controlling the acquisition operation, the angiography device 40 in this exemplary embodiment includes an image processing device 31, which may also be implemented separately, and which is embodied for performing the method.

For this purpose, the image processing device 31 includes a determination unit 32 for determining the angiography dataset 8, which accordingly includes a reconstruction subunit 33 and a backprojection subunit 34. There is further provided in the present example a computing unit 35 for generating the distribution data 6, 7. A distribution unit 36 is provided for performing the distribution of the color intensity of the pixel 11, as well as, optionally, a confidence unit 37 for performing act S5. Further, a visualization unit (not described in more detail) is also conceivable for presenting views of the resulting four-dimensional, corrected angiography dataset 8 on a display device 44.

Also shown is an electronically readable data medium 45 in the form of a CD-ROM on which there is stored a computer program 46 that performs the acts of a method for reducing artifacts when the computer program is executed on the image processing device 31.

Figure 5:
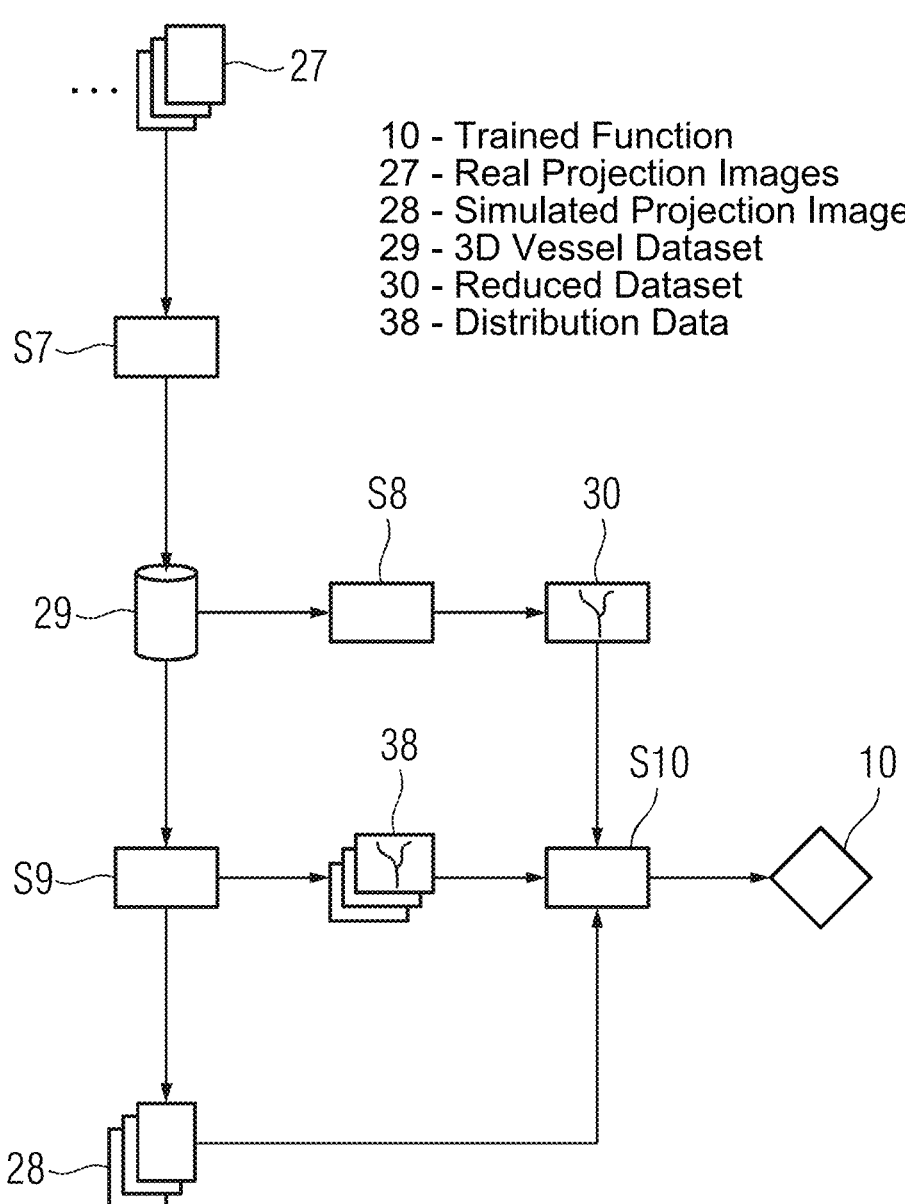
FIG. 5 depicts a flowchart of an embodiment of a computer-implemented method for training a function.

FIG. 5 shows a flowchart of an exemplary embodiment of a computer-implemented method for training a function or for providing the trained function 10. In this exemplary embodiment, real two-dimensional digital subtraction angiography projection images 27, which show a blood circulatory system, and which were acquired at respective time points in a specific time interval, are taken as the starting point. In particular, the projection images 27 may correspond in terms of their type to the projection images 1, 2, 3. A mask image acquired without contrast agent from the respective direction may be subtracted in order to obtain the digital subtraction angiography projection images 27.

In this exemplary embodiment, the projection images 27 show an acquisition region of interest of the blood circulatory system, (e.g., a blood vessel tree of a patient), and, in their temporal sequence, the propagation of the contrast agent which has been administered accordingly in the acquisition region of interest. All of the projection images or a corresponding portion of the projection images 27 are used in act S7 in order to reconstruct herefrom in the customary manner a three-dimensional vessel dataset 29 of the highest possible quality which shows the blood circulatory system in its entirety in the acquisition region. The vessel dataset 29 may contain 3D vessel geometries, the vessel walls of which may serve as a constraining geometry for further method acts. In particular, act S7 of the training method may correspond to act S1 of the method for reducing artifacts.

In an exemplary embodiment, in act S8, a reduced dataset 30 may be determined from the three-dimensional vessel dataset 29, in particular vessel centerlines, which may be generated as first input training data for training the function. This act may correspond in particular to act S2. In terms of its type, the reduced dataset 30 may correspond to the reduced dataset 5.

In the exemplary embodiment shown, the three-dimensional vessel dataset 29 may be generated as input data for a hemodynamic simulation S9 of a virtual blood flow virtually mixed with a contrast agent in the blood circulatory system imaged by the vessel dataset 29, in particular by a simulation computing unit 51 that may be embodied as part of or separately from a training system 47. In particular, a CFD solver may be used for this purpose and a plurality of boundary conditions may be modeled, such as a heart rate, a blood flow rate, a contrast agent injection rate, or the like. In addition or alternatively, clinically measured hemodynamic parameters corresponding to the image datasets may be used for this purpose. In particular, it is possible by the simulation S9 to simulate a distribution of the concentration of the contrast agent in the three-dimensional blood circulatory system imaged by the vessel dataset 29 in a time-resolved manner.

Second input training data, as well as output training data for training the function, may be generated as output data of the hemodynamic simulation S9.

The input training data may therefore include the projection images 28 generated as a result of the simulation S9, which are intended in particular to simulate the real projection images 27 generated, as well as the reduced dataset 30.

The output training data, which may be present in the illustrated relationship to the input training data, may include distribution data 38 relating to a concentration of the contrast agent in the blood circulatory system at the respective time points for the three-dimensional vessel dataset 29 or for the reduced dataset 30.

Finally, in act S10, the function may be trained based on the input training data and the output training data, in particular by a training computing unit 48 of the training system 47. Based on the training, the trained function 10, which may be used for the method for reducing artifacts, may be provided. The trained function 10 may be embodied in a manner as described in relation to FIG. 6 and FIG. 7.

Figure 6:
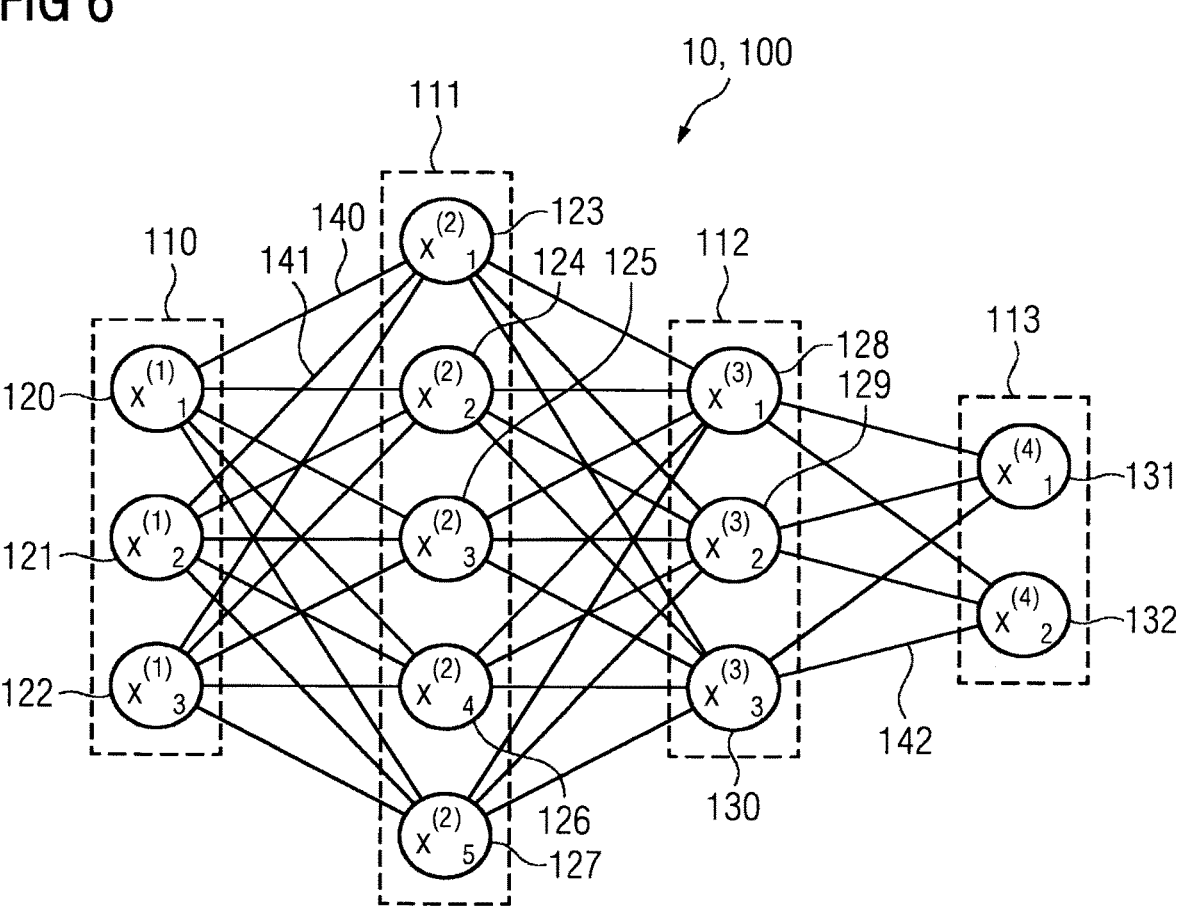
FIG. 6 depicts a schematic representation of an embodiment of an artificial neural network (ANN) of a trained function.

FIG. 6 shows an embodiment variant of an artificial neural network (KNN) 100 for a function or for a trained function 10. Alternative terms for "artificial neural network" are "neural network," "artificial neural net," or "neural net."

The artificial neural network 100 includes nodes 120, . . . , 132 and edges 140, . . . , 142, where each edge 140, . . . , 142 is a directed connection from a first node 120, . . . , 132 to a second node 120, . . . , 132. The first node 120, . . . , 132 and the second node 120, . . . , 132 may be different nodes 120, . . . , 132, though it is also possible that the first node 120, . . . , 132 and the second node 120, . . . , 132 are identical. In FIG. 6, for example, the edge 140 is a directed connection from the node 120 to the node 123, and the edge 142 is a directed connection from the node 130 to the node 132. An edge 140, . . . , 142 from a first node 120, . . . , 132 to a second node 120, . . . , 132 is also referred to as an "inbound edge" for the second node 120, . . . , 132 and as an "outbound edge" for the first node 120, . . . , 132.

In this exemplary embodiment, the nodes 120, . . . , 132 of the artificial neural network 100 may be arranged in layers 110, . . . , 113, where the layers may have an intrinsic order which is introduced by the edges 140, . . . , 142 between the nodes 120, . . . , 132. In particular, the edges 140, . . . , 142 may only exist between neighboring layers of nodes. In the exemplary embodiment shown, there is an input layer 110 which includes only nodes 120, . . . , 122 without incoming edges, an output layer 113, which includes only nodes 131, 132 without outgoing edges, and hidden layers 111, 112 between the input layer 110 and the output layer 113. The number of hidden layers 111, 112 may be chosen arbitrarily. The number of nodes 120, . . . , 122 within the input layer 110 normally relates to the number of input values of the neural network, and the number of nodes 131, 132 within the output layer 113 may relate to the number of output values of the neural network.

In particular, each node 120, . . . , 132 of the neural network 100 may be assigned a (real) number as value. In this case, $x(n)_i$ denotes the value of the i-th node 120, . . . , 132 of the n-th layer 110, . . . , 113. The values of the nodes 120, . . . , 122 of the input layer 110 correspond to the input values of the neural network 100, while the values of the nodes 131, 132 of the output layer 113 correspond to the output value of the neural network 100. Furthermore, each edge 140, . . . , 142 may have a weight that is a real number, the weight being in particular a real number within the interval $[-1, 1]$ or within the interval $[0, 1]$. In this case, $w(m,n)_{i,j}$ denotes the weight of the edge between the i-th node 120, . . . , 132 of the m-th layer 110, . . . , 113 and the j-th node 120, . . . , 132 of the n-th layer 110, . . . , 113. In addition, the abbreviation $w(n)_{i,j}$ is defined for the weight $w(n,n+1)_{i,j}$.

In order to calculate the output values of the neural network 100, the input values are propagated through the neural network. In particular, the values of the nodes 120, . . . , 132 of the (n+1)-th layer 110, . . . , 113 are calculated based on the values of the nodes 120, . . . , 132 of the n-th layer 110, . . . , 113 by:

$$x_j^{(n+1)} = f\left(\sum_i x_i^{(n)} \cdot w_{i,j}^{(n)}\right).$$

In this case, the function f is a transfer function (another term is "activation function"). Known transfer functions are step functions, sigmoid functions (e.g., the logistic function, the generalized logistic function, the hyperbolic tangent, the arcus tangent function, the error function, the smoothstep function), or rectifier functions. The transfer function may be used for normalization.

In particular, the values are propagated layer by layer through the neural network, wherein the values of the input layer 110 are given by the input of the neural network 100, wherein the values of the first hidden layer 111 may be calculated on the basis of the values of the input layer 110 of the neural network, wherein the values of the second hidden layer 112 may be calculated on the basis of the values of the first hidden layer 111, etc.

In order to specify the values w(m,n)I,j for the edges, the neural network 100 is trained with training data. The training data includes training input data and training output data (designated as ti). The neural network 100 is applied to the training input data in a training act in order to generate calculated output data. In particular, the training data and the calculated output data include a number of values corresponding to the number of nodes in the output layer.

In particular, a comparison between the calculated output data and the training data is used in order to adjust the weights within the neural network 100 recursively (back-propagation algorithm). In particular, the weights are varied according to:

$$w_{i,j}^{\prime(n)} = w_{i,j}^{(n)} - \gamma \cdot \delta_j^{(n)} \cdot x_i^{(n)},$$

wherein $\gamma$ is a learning rate, and the numbers $\delta(n)j$ may be calculated recursively as:

$$\delta_j^{(n)} = \left(\sum_k \delta_k^{(n+1)} \cdot w_{j,k}^{(n+1)}\right) \cdot f^\prime\left(\sum_i x_i^{(n)} \cdot w_{i,j}^{(n)}\right)$$

based on $\delta^{(n+1)}_j$ if the (n+1)-th layer is not the output layer, and:

$$\delta_j^{(n)} = \left(x_k^{(n+1)} - t_j^{(n+1)}\right) \cdot f^\prime\left(\sum_i x_i^{(n)} \cdot w_{i,j}^{(n)}\right)$$

if the (n+1)*layer is the output layer 113, where f is the first derivative of the activation function and y(n+1)j is the comparison training value for the $j^{th}$ node of the output layer 113.

Figure 7:
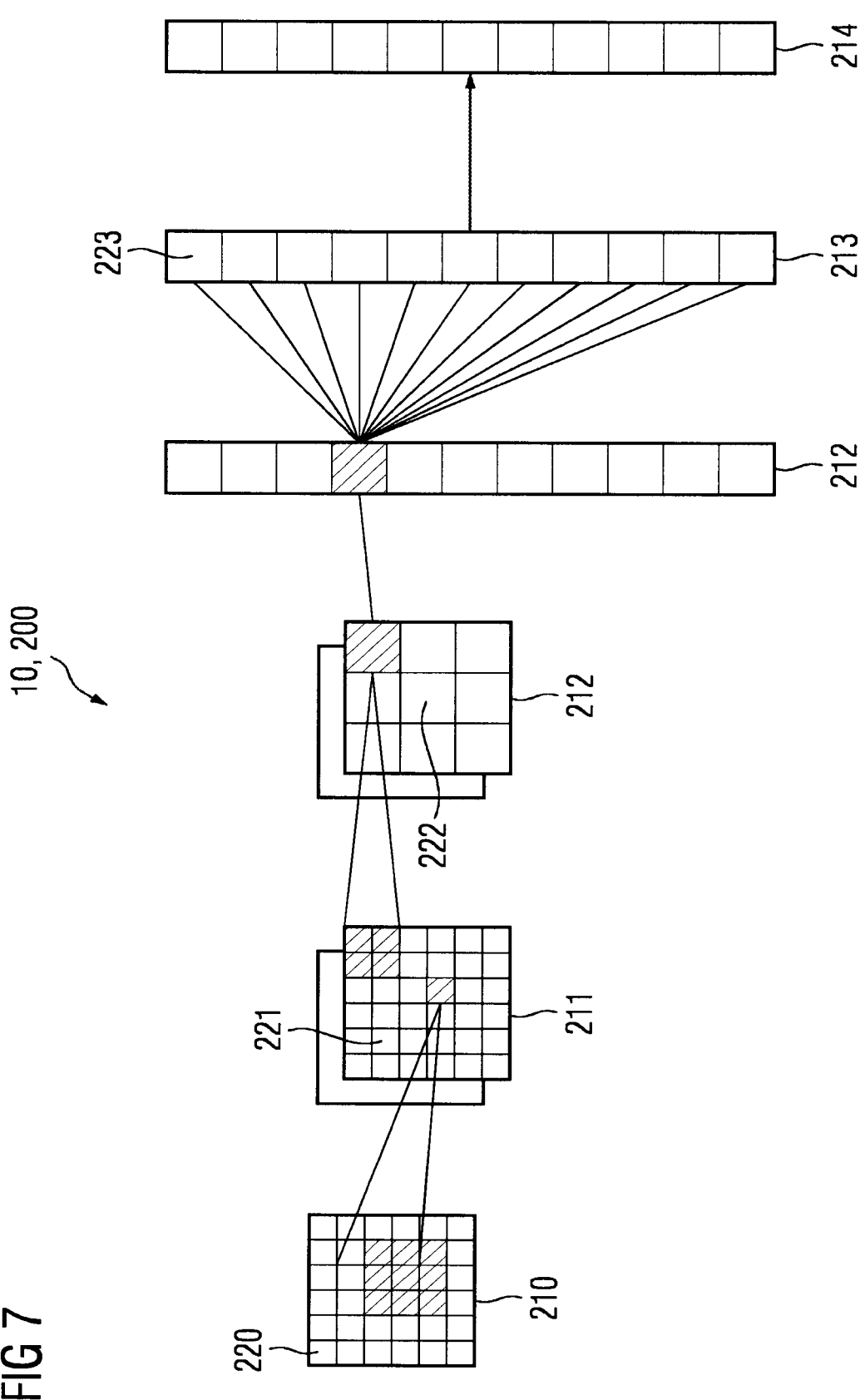
FIG. 7 depicts a schematic representation of an embodiment of an ANN of a trained function.

FIG. 7 shows an embodiment variant of a convolutional neural network 200 for the function or trained function. In the exemplary embodiment shown, the convolutional neural network 200 includes an input layer 210, a convolutional layer 211, a pooling layer 212, a fully connected layer 213, and an output layer 214. Alternatively, the convolutional neural network 200 may also include multiple convolutional layers 211, multiple pooling layers 212, and multiple fully connected layers 213, as well as other types of layers. The order of the layers may be chosen arbitrarily, with fully connected layers 213 normally being used as the last layers before the output layer 214.

In a convolutional neural network 200, the nodes 220, . . . , 224 of a layer 210, . . . , 214 may be regarded as a d-dimensional matrix or as a d-dimensional image. In particular, in the two-dimensional case, the value of the node 220, . . . , 224 indexed with i and j in the n-th layer 210, . . . , 214 may be designated as x(n)[i,j]. However, the arrangement of the nodes 220, . . . , 224 of a layer 210, . . . , 214 has no impact on the calculations performed in the convolutional neural network 200 as such because these are given solely by the structure and the weights of the edges.

A convolutional layer 211 is characterized by the structure and the weights of the inbound edges, which form a convolution operation on the basis of a specific number of kernels. In particular, the structure and the weights of the incoming edges are chosen such that the values $x^{(n)}_k$ of the nodes 221 of the convolutional layer 211 are calculated as a convolution $x^{(n)}_k = K_k * x^{(n-1)}$ on the basis of the values $x^{(n-1)}$ of the nodes 220 of the preceding layer 210, the convolution being defined in the two-dimensional case as:

$$x_k^{(n)}[i, j] = \left(K_k * x^{(n-1)}\right)[i, j] = \sum_{i^\prime} \sum_{j^\prime} K_k[i^\prime, j^\prime] \cdot x^{(n-1)}[i - i^\prime, j - j^\prime].$$

In this case, the k-th kernel $K_k$ is a d-dimensional matrix (in this case, a two-dimensional matrix) that may be small in comparison with the number of nodes 220, . . . , 224 (e.g., a 3×3 matrix or a 5×5 matrix). This means that the weights of the incoming edges are not independent but are chosen such that they result in the convolution equation. In particular for a kernel that is a 3×3 matrix, there are only nine independent weights (each entry in the kernel matrix corresponds to an independent weight) regardless of the number of nodes 220, . . . , 224 in the respective layer 210, . . . , 214. For a convolutional layer 211, the number of nodes 221 in the convolutional layer is in particular equal to the number of nodes 220 in the preceding layer 210 multiplied by the number of kernels.

If the nodes 220 of the preceding layer 210 are arranged as a d-dimensional matrix, the use of a plurality of kernels may be interpreted as adding a further dimension (referred to as a "depth" dimension) such that the nodes 221 of the convolutional layer 221 are arranged as a (d+1)-dimensional matrix. If the nodes 220 of the preceding layer 210 are already arranged as a (d+1)-dimensional matrix with a depth dimension, then the use of multiple kernels may be interpreted as an extension along the depth dimension such that the nodes 221 of the convolutional layer 221 are likewise arranged as a (d+1)-dimensional matrix, the size of the (d+1)-dimensional matrix in relation to the depth dimension being greater by a factor of the number of kernels than in the preceding layer 210.

The advantage of using convolutional layers 211 resides in the fact that a spatially local correlation of the input data may be made use of by enforcing a local connectivity pattern between nodes of neighboring layers, in particular in that each node is connected only to a small section of the nodes of the preceding layer.

In the exemplary embodiment shown, the input layer 210 includes 36 nodes 220, which are arranged as a two-dimensional 6×6 matrix. The convolutional layer 211 includes 72 nodes 221, which are arranged as two two-dimensional 6×6 matrices, each of the two matrices being the result of a convolution of the values of the input layer with a kernel. Equivalently thereto, the nodes 221 of the convolutional layer 211 may be interpreted as a three-dimensional 6×6×2 matrix, the last dimension being the depth dimension.

A pooling layer 212 may be characterized by the structure and the weights of the incoming edges and the activation function of its nodes 222, which form a pooling operation on the basis of a nonlinear pooling function f. In the two-dimensional case, the values $x^{(n)}$ of the nodes 222 of the pooling layer 212 for example may be calculated on the basis of the values $x^{(n-1)}$ of the nodes 221 of the preceding layer 211, as follows:

$$x^{(n)}[i, j] = f\left(x^{(n-1)}[id_1, jd_2], \ldots, x^{(n-1)}[id_1 + d_1 - 1, jd_2 + d_2 - 1]\right)$$

In other words, by using a pooling layer 212, it is possible to reduce the number of nodes 221, 222 by replacing a number d1,d2 of neighboring nodes 221 in the preceding layer 211 by a single node 222, which is calculated as a function of the values of the number of neighboring nodes in the pooling layer. The pooling function f may be the max function, the average, or the L2 norm. In a pooling layer 212, the weights of the incoming edges are fixed and are not changed as a result of the training.

The advantage of using a pooling layer 212 is that the number of nodes 221, 222 and the number of parameters are reduced. This leads to a reduction in the computational overhead in the network and to a validation check on the overfitting.

In the exemplary embodiment shown, the pooling layer 212 is a max pooling in which four neighboring nodes are replaced by just one node, the value being the maximum of the values of the four neighboring nodes. The max pooling operation is applied to each d-dimensional matrix of the preceding layer. In this embodiment variant, the max pooling is applied to each of the two two-dimensional matrices, as a result of which the number of nodes is reduced from 72 to 18.

A fully connected layer 213 may be characterized in that a majority of the edges, in particular all of the edges, between the nodes 222 of the preceding layer 212 and the nodes 223 of the fully connected layer 213 are present, and wherein the weight of each of the edges may be set individually.

In this exemplary embodiment, the nodes 222 of the previous layer 212 of the fully connected layer 213 are represented both as two-dimensional matrices and in addition as non-related nodes (represented as a node line, wherein the number of nodes has been reduced to provide better representability). In this embodiment variant, the number of nodes 223 in the fully connected layer 213 is equal to the number of nodes 222 in the preceding layer 212. Alternatively, the number of nodes 222 and 223 may also be different.

Also in this embodiment variant, the values of the nodes 224 of the output layer 214 are determined by applying the softmax function to the values of the nodes 223 of the preceding layer 213. As a result of applying the softmax function, the sum of the values of all nodes 224 of the output layer is 1, and all the values of all nodes 224 of the output layer are real numbers between 0 and 1. In particular, when the convolutional neural network 200 is used for categorizing input data, the values of the output layer may be interpreted as the probability that the input data falls into one of the different categories.

A convolutional neural network 200 may also contain a ReLU layer (ReLU being an acronym for "rectified linear units"). In particular, the number of nodes and the structure of the nodes in a ReLU layer correspond to the number of nodes and the structure of the nodes in the preceding layer. In particular, the value of each node in the ReLU layer is calculated by applying a rectifier function to the value of the corresponding node of the preceding layer. Examples of rectifier functions are f(x)=max(0,x), the hyperbolic tangent function or the sigmoid function.

Convolutional neural networks 200 may be trained on the basis of the backpropagation algorithm. Regularization methods may be used in order to prevent overfitting, e.g., the omission of nodes 220, . . . , 224, stochastic pooling, use of artificial data, weight reduction on the basis of the L1 or L2 norm or max norm constraints.

Figure 8:
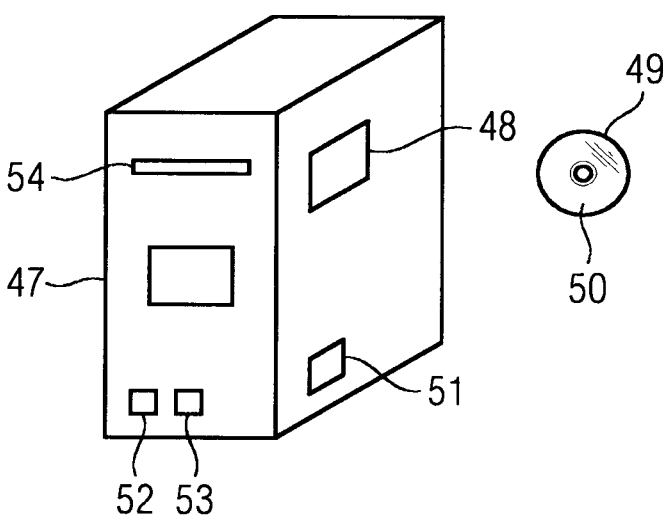
FIG. 8 depicts a schematic representation of an exemplary embodiment of a training system.

FIG. 8 shows a schematic representation of a first exemplary embodiment of a training system 47 having a first training interface 52 configured to receive input training data including two-dimensional digital subtraction angiography projection images 27, 28 showing a blood circulatory system and having been acquired at respective time points in a specific time interval, and a three-dimensional vessel dataset 29 of the blood circulatory system, or a reduced dataset 30 derived therefrom. The training system 47 may include a second training interface 53 configured to receive output training data including distribution data 38 relating to a concentration of a contrast agent in the blood circulatory system at the respective time points for the three-dimensional vessel dataset 29 or for the reduced dataset 30, the output training data being related to the input training data.

The training system 47 may have a training computing unit 48 configured to train a function based on the input training data and the output training data, and a third training interface 54 configured to provide the trained function 10. The training system 47 may optionally include the simulation computing unit 51.

Also shown is an electronically readable data medium 49 in the form of a CD-ROM on which there is stored a computer program 50 configured to perform the acts of a computer-implemented method for providing the trained function 10 when the computer program is executed on the training system 47.

To sum up, it may be said that the fundamental idea behind the proposed method may be interpreted to the effect that the 4D information of the reconstructed series of time-resolved volumes of the angiography dataset may be improved without increasing the contrast agent dose administered to the patient, while the consistency with the acquired projection images is preserved.

In an exemplary embodiment, a trained function may be used to distribute the 2D information from the projection data in the 3D restriction volume in order to reduce the current 4D DSA artifacts (product and prototype) resulting due to vessel overlaps.

Furthermore, the proposed method facilitates the computationally efficient generation of 4D DSA data (angiography dataset), while at the same time the consistency with the input projection data is preserved.

Because a postprocessing act of the 4D DSA flow plausibility check (prototype) is no longer necessary, potential errors caused by this act may be avoided and the reconstruction time may be substantially reduced. Moreover, the confidence value calculation act may be omitted, and the reconstruction time may be significantly shortened.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for reducing artifacts occurring due to vessel overlaps in a four-dimensional angiography dataset, acquired with administration of a contrast agent, of an acquisition region of interest of a blood circulatory system of a patient, wherein a three-dimensional vessel dataset of the blood circulatory system is reconstructed from two-dimensional digital subtraction angiography projection images showing the blood circulatory system and having been acquired at respective time points in a specific time interval, and wherein the four-dimensional angiography dataset is determined by backprojection of the two-dimensional digital subtraction angiography projection images into the three-dimensional vessel dataset, the method comprising:

generating distribution data relating to a concentration of the contrast agent in the blood circulatory system at the respective time points for the three-dimensional vessel dataset or for a reduced dataset derived therefrom, wherein the distribution data is generated as output data of a trained function, and wherein the trained function is applied to the two-dimensional digital subtraction angiography projection images and the three-dimensional vessel dataset or the reduced dataset as input data; and distributing a color intensity of a pixel of a respective two-dimensional digital subtraction angiography projection image of the two-dimensional digital subtraction angiography projection images, wherein the pixel shows a contrast agent filling state according to the distribution data at a respective time point of the two-dimensional digital subtraction angiography projection image across voxels of the three-dimensional vessel dataset that lie along a ray associated with the pixel in the backprojection.

2. The method as claimed in claim 1, further comprising:

determining a number of voxels lying on the ray from the three-dimensional vessel dataset; and assigning a measure for the determined number to the voxels, wherein the color intensity of the pixel is distributed according to the distribution data when the measure falls below a predefined value.

3. The method of claim 2, further comprising:

determining vessel centerlines of the blood circulatory system as the reduced dataset from the three-dimensional vessel dataset, wherein the distribution data relating to the concentration of the contrast agent in the blood circulatory system is generated for the vessel centerlines.

4. The method of claim 3, wherein the distribution data relating to the concentration of the contrast agent for the vessel centerlines is extrapolated onto the three-dimensional vessel dataset.

5. The method of claim 1, further comprising:

determining vessel centerlines of the blood circulatory system as the reduced dataset from the three-dimensional vessel dataset, wherein the distribution data relating to the concentration of the contrast agent in the blood circulatory system is generated for the vessel centerlines.

6. The method of claim 5, wherein the distribution data relating to the concentration of the contrast agent for the vessel centerlines is extrapolated onto the three-dimensional vessel dataset.

7. The method of claim 1, wherein the trained function is generated by a computer-implemented method comprising:

receiving input training data comprising: (1) two-dimensional digital subtraction angiography projection images showing the blood circulatory system and having been acquired at respective time points in a specific time interval; and (2) a three-dimensional vessel dataset of the blood circulatory system or a reduced dataset derived therefrom;

receiving output training data comprising distribution data relating to a concentration of the contrast agent in the blood circulatory system at the respective time points for the three-dimensional vessel dataset or for the reduced dataset, wherein the output training data is related to the input training data;

training a function based on the input training data and the output training data, wherein the output data is generated by applying the function to the input training data and parameters of the function are adjusted based on a comparison of the output data with the output training data; and providing the trained function.

8. The method of claim 1, wherein the distribution data relating to the concentration of the contrast agent is generated as the output data of a hemodynamic simulation of a virtual blood flow virtually mixed with the contrast agent in the blood circulatory system reconstructed by the three-dimensional vessel dataset.

9. A computer-implemented method for providing a trained function, the computer-implemented method comprising:

receiving input training data comprising:

two-dimensional digital subtraction angiography projection images showing a blood circulatory system and having been acquired at respective time points in a specific time interval; and a three-dimensional vessel dataset of the blood circulatory system or a reduced dataset derived therefrom;

receiving output training data comprising distribution data relating to a concentration of a contrast agent in the blood circulatory system at the respective time points for the three-dimensional vessel dataset or for the reduced dataset, wherein the output training data is related to the input training data;

training a function based on the input training data and the output training data, wherein output data is generated by applying the function to the input training data and parameters of the function are adjusted based on a comparison of the output data with the output training data; and providing the trained function.

10. The computer-implemented method of claim 9, wherein the output training data is generated as output data of a hemodynamic simulation of a virtual blood flow virtually mixed with the contrast agent in the blood circulatory system imaged by the three-dimensional vessel dataset.

11. The computer-implemented method of claim 10, wherein the two-dimensional digital subtraction angiography projection images are generated as further output data of the hemodynamic simulation, and wherein the two-dimensional digital subtraction angiography projection images simulate real projection images acquired in a real digital subtraction angiography procedure.

12. The computer-implemented method of claim 9, wherein vessel centerlines of the blood circulatory system are determined as the reduced dataset from the three-dimensional vessel dataset, and wherein the distribution data relating to the concentration of the contrast agent in the blood circulatory system is provided for the vessel centerlines.

13. An image processing device comprising:

a determination unit configured to determine a four-dimensional angiography dataset, acquired with administration of a contrast agent, of an acquisition region of interest of a blood circulatory system of a patient, having a reconstruction subunit for reconstructing a three-dimensional vessel dataset of the blood circulatory system from two-dimensional digital subtraction angiography projection images showing the blood circulatory system and having been acquired at respective time points in a specific time interval, and a backprojection subunit for determining the four-dimensional angiography dataset by backprojection of the two-dimensional digital subtraction angiography projection images into the three-dimensional vessel dataset;

a computing unit configured to generate distribution data relating to a concentration of the contrast agent in the blood circulatory system at the respective time points for the three-dimensional vessel dataset or for a reduced dataset derived therefrom, wherein the distribution data is generated as output data of a trained function, and wherein the trained function is applied to the two-dimensional digital subtraction angiography projection images and the three-dimensional vessel dataset or the reduced dataset as input data; and a distribution unit configured to distribute a color intensity of a pixel of a respective two-dimensional digital subtraction angiography projection image of the two-dimensional digital subtraction angiography projection images, wherein the pixel shows a contrast agent filling state according to the distribution data at a respective time point of the two-dimensional digital subtraction angiography projection image across voxels of the three-dimensional vessel dataset that lie along a ray associated with the pixel in the backprojection.

14. A training system configured to provide a trained function, the training system comprising:

at least one processor configured to:

receive input training data comprising: (1) two-dimensional digital subtraction angiography projection images showing a blood circulatory system and having been acquired at respective time points in a specific time interval; and (2) a three-dimensional vessel dataset of the blood circulatory system or a reduced dataset derived therefrom;

receive output training data comprising distribution data relating to a concentration of a contrast agent in the blood circulatory system at the respective time points for the three-dimensional vessel dataset or for the reduced dataset, wherein the output training data is related to the input training data;

train a function based on the input training data and the output training data, wherein output data is generated by applying the function to the input training data and parameters of the function are adjusted based on a comparison of the output data with the output training data; and provide the trained function.

* * * * *